US00PP21752P3

(12) United States Plant Patent
Merritt

(10) Patent No.: US PP21,752 P3
(45) Date of Patent: Mar. 1, 2011

(54) LILY PLANT NAMED 'BJM 004'

(50) Latin Name: ***Lilium Asiatic×L. longiflorum* hybrid**
Varietal Denomination: BJM 004

(75) Inventor: Richard H. Merritt, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 200 days.

(21) Appl. No.: 12/287,592

(22) Filed: Oct. 10, 2008

(65) Prior Publication Data

US 2010/0095418 P1 Apr. 15, 2010

(51) Int. Cl.
*A01H 5/00* (2006.01)

(52) U.S. Cl. ..... Plt./314

(58) Field of Classification Search ..... Plt./314
See application file for complete search history.

(56) References Cited

U.S. PATENT DOCUMENTS

PP16,360 P2 * 3/2006 Mak ..... Plt./314

* cited by examiner

*Primary Examiner*—Wendy Haas
(74) *Attorney, Agent, or Firm*—Klarquist Sparkman, LLP

(57) ABSTRACT

A new and distinct lily plant substantially as shown and described, characterized by (1) stem thickness supported by flower crown without bending (9 mm in diameter); (2) straight stems with even leaf distribution from bottom to top (102 leaves per plant); (3) flower crown compact (around 12×12 cm); (4) flower sizes large (11-14 cm long 11-14 cm wide at open stage); (5) continuous blooms for two to four weeks; (6) coloration of leaves uniform from bottom to top; (7) height of plant around 30 cm; and (8) red flowers.

4 Drawing Sheets

Latin name of the genus and species of the plant claimed: *Lilium Asiatic×L. longiflorum* hydrid.

Botanical name—variety denomination: 'BJM 004'.

CROSS REFERENCE TO RELATED APPLICATIONS

This application is related to U.S. application Ser. No. 12/287,591.

STATEMENT REGARDING FEDERALLY SPONSORED RESEARCH OR DEVELOPMENT

None.

FIELD

The present invention comprises a new and distinct cultivar of *Lilium* named 'BJM 004' characterized by large snowy red flower crowns on strong stems with rich green foliage. This cultivar is winter hardy, sprouts freely and can provide a short garden/specimen plant of up to 10 blooms.

SUMMARY

A new and distinct cultivar of *Lilium Asiatic×L. longiflorum* hybrid named 'BJM 004' substantially as herein shown and described in FIGS. 1-4. The parentage of the new *longiflorum* variety is not known, the parentage of the *Asiatic* parent is 'Little Missy' (unpatented). The variety was developed as part of a breeding program in New Brunswick, N.J.

The new variety is characterized by numerous red compact flower crowns on short straight strong stems with rich green plentiful foliage. The following traits have been repeatedly observed in asexually propagated progeny and are determined to be the basic characteristics of this invention which in combination distinguish this lily as a new and distinct cultivar: (1) stem thickness supported by flower crown without bending (9 mm in diameter); (2) straight stems with even leaf distribution from bottom to top (102 leaves per plant); (3) flower crown compact (around 12×12 cm); (4) flower sizes large (11-14 cm long 11-14 cm wide at open stage); (5) continuous blooms for two to four weeks; (6) coloration of leaves uniform from bottom to top; (7) height of plant around 30 cm; and (8) red flowers. To the inventor's knowledge, there are no other cultivars of lily of this size of plant or in terms of the superior plant and flower quality in the market.

'BJM 004' has been asexually reproduced by tissue culture using bulb scale in New Brunswick, N.J. No evidence of off-types of 'BJM 004' have been observed or reported to us. Thus, it is concluded that 'BJM 004' is stable and reproduces true to type in successive generations of asexual reproduction.

The following detailed description concerns the variety 'BJM 004'. Progeny of the original plant have been observed growing in cultivated areas in New Brunswick, N.J. Certain characteristics of this variety, such as growth and color, may change with changing environmental conditions (such as light, temperature, moisture, nutrient availability, soil or other factors). Color descriptions and other terminology are used in accordance with their horticultural descriptions, unless the context clearly indicates otherwise. Color designations are used with reference to the Munsell Color Charts for Plant Tissues.

Figure 1:
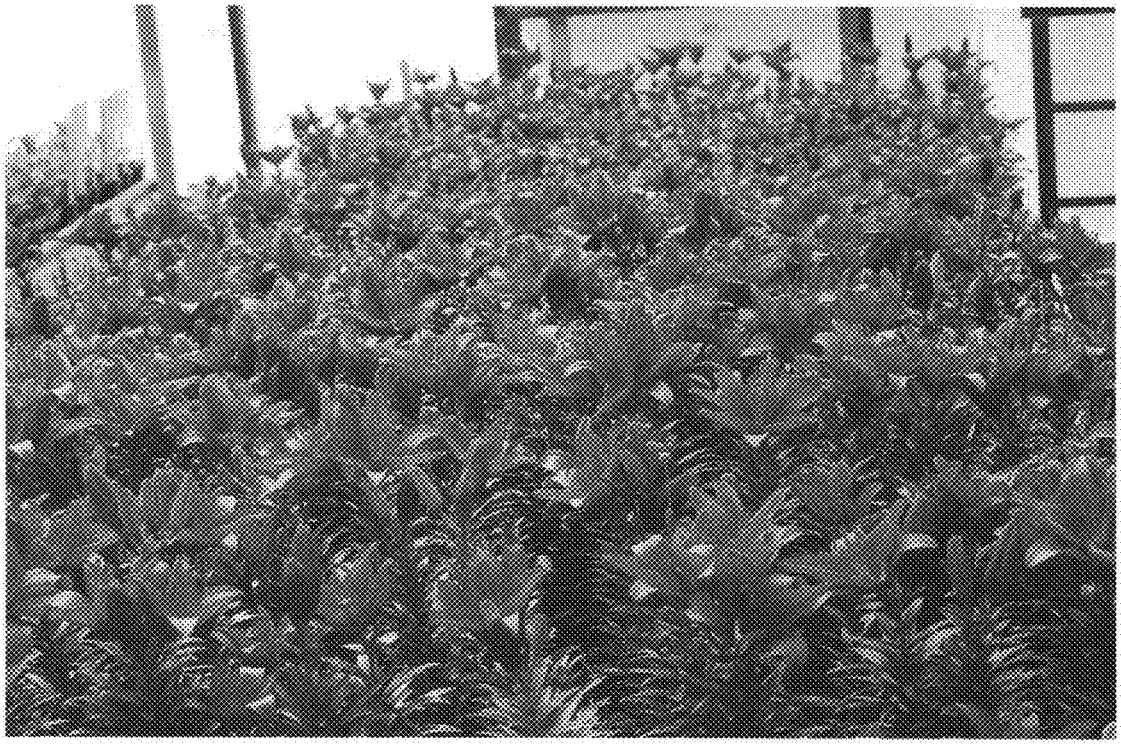
FIG. 1 is a photograph showing several plants of the new variety.
Figure 2:
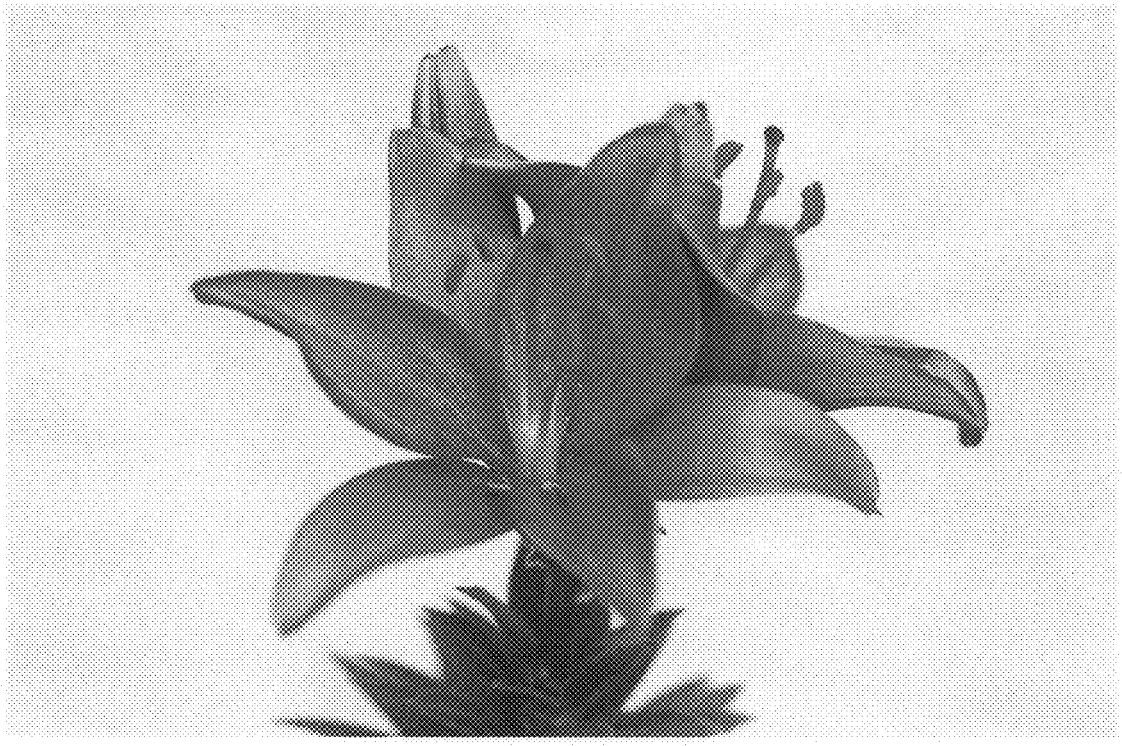
FIG. 2 is a photograph showing a close-up of the flowers of the new variety.
Figure 3:
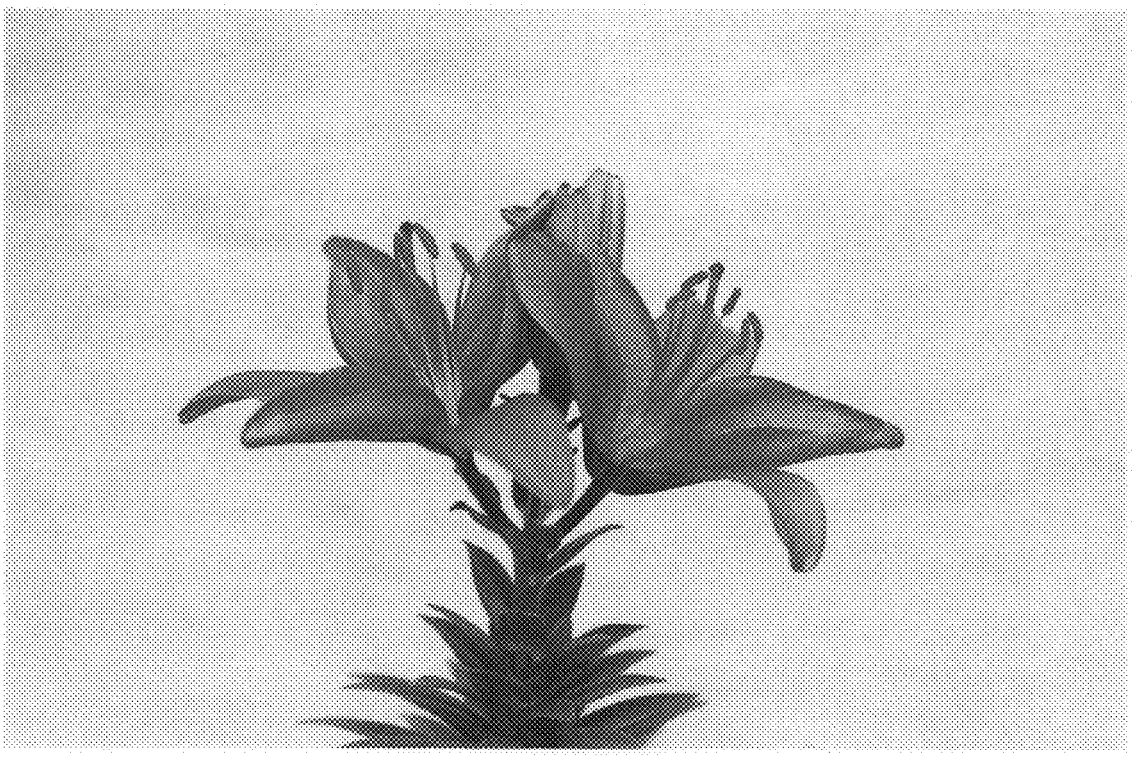
FIG. 3 is a photograph showing a close-up of the flowers the new variety.
Figure 4:
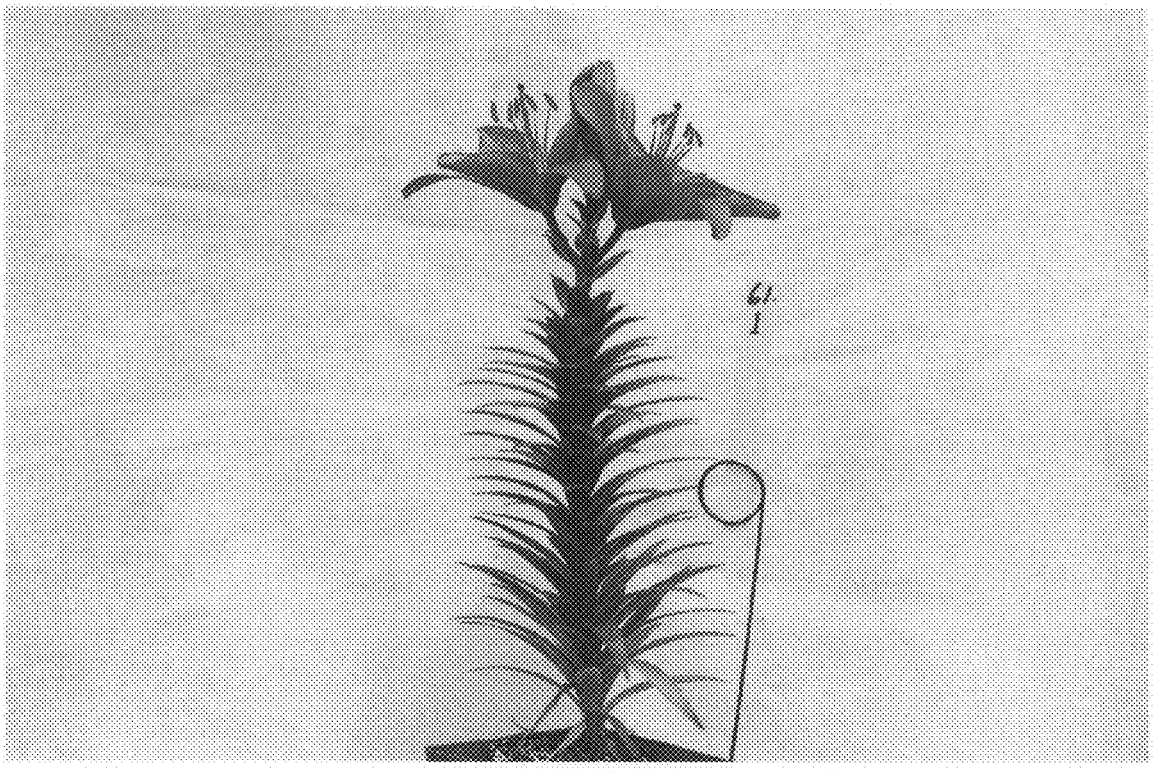
FIG. 4 is a photograph showing the stalk of the new variety.

The colors of an illustration of this type may vary with lighting and other conditions and, therefore, color characteristics of this new variety should be determined with reference to the observations described herein, rather than from this illustration alone.

BOTANICAL DESCRIPTION

The following is a detailed description of the invention based on lily plant 'BJM 004' produced under asexual reproduction by tissue culturing. Characteristics based on observations of a nine-month-old plant.

I. Relating to the plant:

*Origin.*—New Brunswick, N.J.

*Parentage.*—*Lilium Asiatic* 'Little Missy'×*L. longiflorum* hybrid.

*Seed parent.*—*L. Asiatic* 'Little Missy' (unpatented).

*Pollen parent.*—*L. longiflorum* hybrid.

*Commercial classification.*—Bedding, specimen plant.

*Classification.*—Division 5, according to the Horticultural Classification of Lilies by The Royal Horticultural Society of London.

*Height.*—Approximately 30 cm. from the top of the soil to the top of the flowers from bulbs of 12 cm in circumference.

*Stem color.*—Green-yellow — Munsell 5 GY, V5/C4-6.

*Stem diameter.*—9 mm.

*Foliage.*—102 leaves.

*Leaf arrangement.*—Staggered upright.

*Leaf size.*—Approximately 6 cm long 1.3 cm wide.

*Texture.*—Smooth.

*Color.*—Green-yellow — Munsell 5GY V4/C6.

*Color.*—White.

*USDA Zone.*—Winter hardy to USDA zone 6.

II. The bud:

*Size.*—6 cm long and 2 cm wide just prior to opening.

*Color.*—Red — Munsell 5RP V4/C10.

III. The flower:

*Blooming habit.*—Terminal inflorescence.

*Days to bloom.*—Flowers approximately 84 days after spring greenhouse planting (70-78° F. during the day, 60-70° F. at night) under typical commercial flower forcing conditions of 16° Celsius night time temperatures.

*Inflorescence size.*—Approximately 11 cm to 14 cm high and 11 cm to 14 cm wide when there are 3 flowers present.

*Flower size.*—Large.

*Diameter.*—Approximately 11 cm.

*Depth.*—Approximately 6 cm to 6.5 cm.

*Tepal number.*—6.

*Flower color.*—Inner color red shades — 5R, V3/C6; outer color: 5R, V4/C8-10 Munsell.

*Tepal shape.*—Slight cup, inner; tip bent outward.

*Texture.*—Shiny/matte finish.

IV. The reproductive organs:

*Number.*—6.

*Anthers before dehiscence.*—Approximately 1 cm. Color: red shades — 10R, V4/C10 Munsell.

*Filaments.*—Length: approximately 5.2 cm; Color: red shades — 5RP V5/C10, bottom fades to 5YR V8/C4 Munsell.

*Pollen.*—Color: yellow — 2.5Y V8/C10 Munsell.

*Pistil.*—Exserted beyond stamens.

*Number.*—1.

*Style.*—Length: approximately 4.5 cm; Color: red — 10R V4-C8 Munsell.

*Stigma.*—Color: yellow-red — 5YR, V3/C2 Munsell.

V. The fruit:

*Fertility.*—None.

TABLE 1

Comparison of 'BJM 004' to other varieties

| | Parent *L. Asiatic* 'Little Missy' | Parent *L. longiflorum* hybrid (2-1 × 4-8) | 'BJM 004' (61-1) | 'BJM 005' (61-2) |
|---|---|---|---|---|
| Plant Height | 25 cm | 27 cm | 30 cm | 40 cm |
| Flower color | Dark pink, speckled with white marks on petals | White (RHSCC Group 155B) | Red (5R V4/C8-10) | Red/Purple (RP V4-5/C8-10) |
| Leaf Count | 80 | 55 avg | 102 avg. | 115 avg. |
| Days to bloom | 120 days | 127 days | 84 days | 90 days |
| Rebloom fall | No | No | Yes | No |
| Rebloom spring | No | Yes | Yes | Yes |

I claim:

1. A new and distinct lily plant as herein illustrated and described.

* * * * *